US00PP08234P

United States Patent [19]

Sommerfeld, III

[11] Patent Number: Plant 8,234

[45] Date of Patent: May 18, 1993

[54] "SOMMERFELD" APPLE TREE

[76] Inventor: August E. Sommerfeld, III, 21713 Lake Rd., La Grange, Calif. 95329

[21] Appl. No.: 833,120

[22] Filed: Feb. 10, 1992

[51] Int. Cl.[5] ..... A01H 5/00
[52] U.S. Cl. ..... Plt./34.1
[58] Field of Search ..... Plt./34.1

*Primary Examiner*—James R. Feyrer
*Attorney, Agent, or Firm*—Worrel & Worrel

[57] ABSTRACT

A new and distinct variety of apple tree which is somewhat remotely similar to the "Royal Gala" apple tree (U.S. Plant Pat. No. 4,121) and "Fuji" apple tree (non-patented) from which it is believed derived, but from which it is distinguished by producing fruit which are mature for harvesting and shipment approximately three-and-one half weeks later than the fruit produced by the "Royal Gala" apple tree and about five weeks prior to the fruit produced by the "Fuji" apple tree. The fruit of the new variety of apple tree is of excellent quality being of semi-blushed coloration, conical to slightly oblate shape and having a very sweet flavor.

1 Drawing Sheet

BACKGROUND OF THE NEW VARIETY

The present invention relates to a new and distinct variety of apple tree which will hereinafter be denominated varietally as the "Sommerfeld apple tree", and, more particularly, to an apple tree which produces fruit which are mature for commercial harvesting and shipment approximately September 7 to September 20 near La Grange in the central valley of California, and which further is distinguished by producing an attractive, sesmi-blushed fruit, having an excellent sweet flavor and producing regular crops of large fruit in mid season.

The climatic conditions prevailing in the central valley of California limit the number of commercial varieties of apple trees which can successfully be grown to produce commercially acceptable fruit. The hot, arid conditions during the summer months coupled with relatively few days each year in which chilling conditions are reached are not favorable to many varieties of apple trees which can be grown successfully under more conducive growing conditions.

However, two commercial varieties of apple trees perform well under these otherwise adverse conditions. The "Fuji" apple tree (unpatented) has fruit resembling that of the "Delicious" apple tree in color and otherwise being of commercially acceptable quality tolerant of the growing conditions in the central valley of California. The color of the fruit is essentially green with occasional fruit, usually that growing near the exterior of the tree, displaying a pink striping or blush. The fruit of the "Fuji" apple tree ripened for harvest near La Grange, Calif. approximately from Oct. 5 to Oct. 16 in 1991.

The other of the two commercial varieties tolerant of these growing conditions is the "Royal Gala" apple tree (U.S. Plant Pat. No. 4,121). The "Royal Gala" apple tree produces fruit having a red blush exterior coloration. In 1991 near La Grange, Calif. the fruit reached maturity from approximately Aug. 4 to Aug. 16. As a consequence of the limited number of such commercial varieties tolerant of these growing conditions, the industry has a long recognized need for new varieties which can thrive under such growing conditions, particularly if they produce fruit ripening for harvest at periods compatible with existing varieties and having high skin coloration.

ORIGIN AND ASEXUAL REPRODUCTION OF THE NEW VARIETY

The new and distinct variety of apple tree hereof was a chance seedling discovered by the inventor in a cultivated area on property at 21713 Lake Road in La Grange, Calif. which is the inventor's residence. The orchard in which it was found was established in early 1981 or 1982 by the inventor and included pear trees, peach trees, fig trees as well as apple trees. The varieties of apple trees planted were "Golden Delicious", "Royal Gala", "Anna" or "Honest" and "Fuji". Subsequently, the trees were badly damaged by grasshoppers and lack of proper irrigation. Seedlings which thereafter grew in the orchard were left in place by the inventor as possible replacements for the damaged trees.

The parent tree of the new variety of the present invention was discovered by the inventor as a chance seedling in June 1984 beneath one of the "Fuji" apple trees in the orchard. As it produced fruit, the inventor discovered that it matured earlier than the fruit of the "Fuji" apple tree and after that of the "Royal Gala" apple tree. The new variety is believed to be derived from the "Fuji" and "Royal Gala" apple trees. The new variety was first asexually reproduced at the inventor's direction in 1987 by grafting cuttings onto M 111 rootstock. The trees were planted on the same property on which the new variety was discovered. The inventor continued to observe the asexually reproduced trees of the new variety and confirmed that they possessed the same distinctive characteristics as the parent tree thereof.

SUMMARY OF THE NEW VARIETY

The "Sommerfeld" apple tree is characterized as to novelty by producing an earlier maturing and more highly colored fruit than that of the "Fuji" apple tree having attractive large fruit which have an excellent sweet flavor. The fruit of the "Sommerfeld" apple tree is ripe for commercial harvesting and shipment approximately September 7 to September 20 in La Grange in the central valley of California. The new variety is most closely similar to the "Royal Gala" apple tree (U.S. Plant Pat. No. 4,121) and the "Fuji" apple tree (unpatented) from which it is believed it was derived as a chance seedling, but from which it is distinguished and characterized principally as to novelty by producing fruit which are ripe for harvesting and shipment approximately three-and-one half weeks after the "Royal Gala" apple tree and approximately five weeks prior to the "Fuji" apple tree and which further produces a fruit having color which is a substantial improvement over the parent, "Fuji" apple tree.

The "Fuji" apple tree produces fruit which is essentially green with occasional fruit displaying a pink striping or blush. In the warmer areas of the central valley of California, this blush usually covers less than twenty-five percent (25%) of the fruit surface. In contrast, the exterior fruit of the new variety, under similar circumstances, can have as much as eighty percent (80%) of the fruit surface covered with red blush. In comparison with the "Royal Gala" apple tree, the fruit of the new variety usually has an equal or higher percentage of exterior red blush present. The shape of the fruit of the new variety is conical to slightly oblate in the side or lateral view. This is in contrast to the fruit of the "Fuji" variety which most often is strongly oblate. The fruit shape of the new variety is, however, less elongate laterally than that of the "Royal Gala" variety. The fruit form of both the new variety and the "Royal Gala" variety fall into the "conical" category.

The fruit of the new variety is of excellent quality. It is very sweet being most similar to that of its "Fuji" parent whose superior quality is well known. In comparison, the fruit of the "Royal Gala" variety, also has a high quality apple, develops more acidicy than does the fruit of the new variety.

BRIEF DESCRIPTION OF THE DRAWING

The accompanying drawing is a color photograph of four mature fruit of the subject variety, one of which has been divided in the axial plane and laid open to show the flesh and seed characteristics thereof, two others of which are shown in top plan view and a last of which is shown in side elevation, all of which are sufficiently matured for harvesting and shipment, together with a shoot bearing representative leaves which display the ventral and dorsal coloration thereof.

DETAILED DESCRIPTION

Referring more specifically to the pomological details of this new and distinct variety of apple tree, the following has been observed under the ecological conditions prevailing at the applicant's orchard of origin which is located in LaGrange, Calif. All major color code designations are by reference to the Dictionary of Color, by Maerz and Paul, Second Edition, 1950. Common color names are also occasionally employed.

TREE

Generally:

*Size.*—Average.

*Vigor.*—Vigorous. The tree is hardy under climatic conditions typical of the central valley of California.

*Figure.*—Upright. Tree form and density can be substantially modified by pruning.

*Productivity.*—Productive.

*Regularity of bearing.*—Regular.

Trunk:

*Size.*—Average diameter.

*Surface texture.*—Average.

*Color.*—Medium brown (Cordova brown 7-J-11) and at times overlain with a light greyish caste.

*Lenticels.*—Numbers — Numerous.

Branches:

*Size.*—Average in thickness.

*Surface texture.*—Relatively smooth.

*Color — one year or older wood.*—Reddish brown (Laurel Oak 7-J-10) to a more brown-green (Clove brown 15-C-12). Most mature shoots have numerous light colored lenticels present. Smaller shoots are often covered with a light matted grey pubescence.

*Color — immature shoots.*—Range from a light grey-green (17-D-6) for the least mature, darkening eventually to a reddish brown (Tanagra brown 7-J-9) for the most mature. All immature shoots are heavily covered with a short dense grey pubescence.

LEAVES

Size:

*Generally.*—Medium to large.

*Average length.*—Leaf measurements taken from leaves growing at the midpoint of upright, vigorous, current season's shoots. 13.4 cm (34.036 inches) including the leaf petiole.

*Average width.*—6.6 cm (16.764 inches).

Form: Elliptical. Apex leaf apex acute with the apex at times slightly twisted sideways.

Color:

*Upwardly disposed surface.*—Dark green (24-H-9).

*Downwardly disposed surface.*—A much lighter grey-green (22-F-5).

The young leaves at shoot terminals are frequently an even lighter yellow-green (19-K-5).

Marginal form:

*Generally.*—Somewhat coarsely serrate, often doubly so. Serrations are medium to large in size.

Petiole:

*Size.*—Medium.

*Length.*—28 mm (1.102 inches) to 30 mm (1.181 inches).

*Thickness.*—2 mm (0.0787 inches).

*Color.*—Grey-green (20-H-5). The basal portion of the petiole is often tinged with reddish coloration. The leaf petiole is covered with a short matted pubescence.

Stipules:

*Generally.*—Persistent throughout the growing season.

*Form.*—Linear lanceolate.

*Margin.*—Sparsely serrate with small, widely spaced serrations.

*Color — upper surface.*—Dark green (23-H-8).

*Color — downward surface.*—Lighter grey-green (21-G-5).

*Size.*—Medium to large.

*Length.*—16 mm (0.0629 inches) to 21 mm (0.8267 inches).

*Width.*—3 mm (0.1181 inches) to 6 mm (0.2362 inches).

FLOWERS

Flower buds:

*Size.*—Medium.

*Form.*—Conic.

*Surface texture.*—Pubescent.

*Color.*—Dark chestnut brown (Nomad brown 8-L-10).

Flowers:

*Generally.*—Abundant. Most commonly five flowers per spur bud.

Date of bloom: Mid season in timing, with bloom reaching full stage on Mar. 10, 1991. Bloom at La Grange, Calif. was relatively long in 1991, lasting over a three week period. The bloom of the new variety roughly overlapped that of the "Fuji" apple tree of the parent variety in 1991. The number of hours of chilling below 45 degrees F. in any specific year, however, can impact both the length and onset of bloom.

Size:

*Generally.*—Medium. Diameter 31 mm (1.220 inches) when fully open.

Petals:

*Number.*—Usually five.

*Color.*—Light pink (1-B-1).

*Form.*—Oval to ovate.

*Length.*—22 mm (0.0866 inches).

*Width.*—10 mm (0.3937 inches).

*Margin.*—Moderately undulate.

Pollen: Abundant.

*Color.*—Yellow (10-L-3).

FRUIT

Maturity when described: Ripe for commercial harvesting and shipment approximately September 7 to September 20 in La Grange, Calif.

Size:

*Generally.*—Large with good uniformity.

*Larger fruit — average diameter in the axial plane.*—76 mm (2.992 inches) to 82 mm (3.228 inches).

*Larger fruit — average cheek diameter.*—85 mm (3.346 inches) to 90 mm (3.543 inches).

*Smaller fruit — average diameter in axial plane.*—60 mm (2.362 inches) to 65 mm (2.559 inches).

*Smaller fruit — average cheek diameter.*—75 mm (2.952 inches) to 82 mm (3.228 inches).

Form:

*Uniformity.*—Somewhat variable from conical to slightly oblate in lateral aspect. Globose in cross-sectional aspect.

Stem cavity:

*Generally.*—Medium.

*Width.*—Moderately wide.

*Depth.*—Moderately deep, 17 mm (0.6692 inches) to 23 mm (0.9055 inches).

*Angle.*—Acute.

*Shape.*—Cavity shoulder is rounded.

Stem:

*Generally.*—Medium.

*Length.*—25 mm (0.9842 inches) to 29 mm (1.141 inches).

*Thickness.*—Variable. Diameter 2.0 mm (0.0787 inches) to 3.5 mm (0.1377 inches).

*Color.*—Most often a light green (Biscay green 21-K-5). Often with some areas blotched with brown (14-G-7).

Skin:

*Surface.*—Moderately waxy. Numerous relatively small inconspicuous dots are present, slightly areolar in form with calloused surface. The surface dots are light in color and more numerous over the apex and more scattered over the basal shoulders. The skin is usually covered with a light greyish colored bloom.

*Texture.*—Medium.

*Flavor.*—Neutral.

*Blush color.*—At times, the pattern is striped in form from a slightly dull dark red (Chalet red 6-K-10) to a lighter red (Sanoa red 6-F-11). Other times, the blush color occurs in more of a washed pattern within the same range of red coloration. On many fruit both color patterns are present. The blush can cover up to 80 percent of the fruit surface especially on fruit that is borne on the exterior portion of the tree and is exposed to direct sunlight. Interior fruit are much less likely to be highly blushed, at times down to 15 to 20 percent of the fruit surface.

*Ground color.*—Varies from a light yellow (9-K-1) to a yellow-green (18-K-3).

*Surface color.*—Variable in development.

Flesh:

*Juice production.*— *Juicy.*

*Flavor.*—Sweet, mild and very well balanced.

*Flesh texture.*—Medium grained, relatively tender.

*Flesh color.*—Very light yellow-cream (9-D-1) throughout.

*Eating quality.*—Excellent.

Core:

*Size.*—Medium.

*Generally.*—Median in position within the fruit. The core lines are most frequently clasping, but only slightly below the tip of the calyx tube. The seed cavities within the core are substantially closed. Carpels are distinctly emarginate in form. Carpel surface is smooth.

Basin:

*Size.*—Medium and relatively shallow, from 8 mm (0.3149 inches) to 9 mm (0.3543 inches) deep. Basin shoulder is low and rounded. The basin surface is waxy, with gentle but irregular undulations.

Calyx:

*Size.*—Relatively small.

*Form.*—Closed to very slightly open.

*Lobes.*—Separated and usually distinctly reflexed; pubescent with moderately long and matted pubescence.

*Tube.*—Relatively short and moderately wide. The tube is cone shaped.

Stamens: Attached quite basally within the calyx tube.

Seeds: Numerous, most frequently one per carpel, 5 total.

*Color.*—Dark brown (Maracaibo brown 8-L-9).

Use: Fresh market.

Keeping quality: Appears to be substantially as is the fruit of the "Fuji" apple tree.

Although the new variety of apple tree possesses the described characteristics noted above as a result of the growing conditions prevailing near La Grange, Calif., it is to be understood that variations of the usual magnitude and characteristics incident to changes in growing conditions, irrigation, fertilization, pruning and pest control are to be expected.

Having thus described and illustrated my new variety of apple tree, what I claim as new and desire to be secured by Plant Letters Patent is:

1. A new and distinct variety of apple tree substantially as illustrated and described which is similar to the "Royal Gala" apple tree (U.S. Plant Pat. No. 4,121) and "Fuji" apple tree (unpatented) from which it is believed derived and with which it is most closely similar, but from which it is distinguished by producing fruit which are mature for commercial harvesting and shipment approximately three-and-one half weeks later than the fruit of the "Royal Gala" apple tree and about five weeks prior to the fruit of the "Fuji" apple tree in the central valley of California and which is very sweet and of excellent quality.

* * * * *

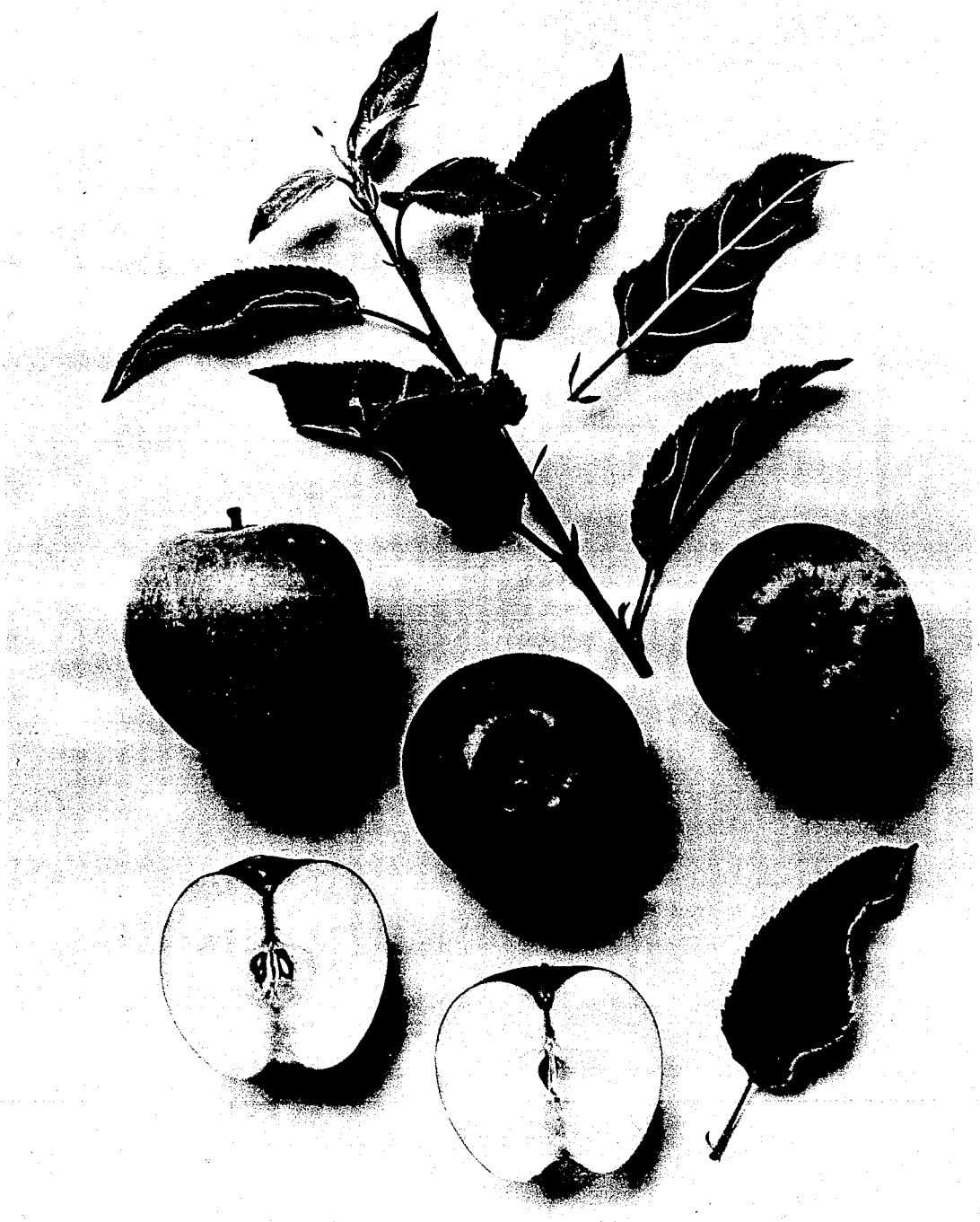

UNITED STATES PATENT AND TRADEMARK OFFICE

CERTIFICATE OF CORRECTION

PATENT NO. : PP: 8,234

DATED : May 18, 1993

INVENTOR(S) : August E. Sommerfeld, III

It is certified that error appears in the above-identified patent and that said Letters Patent is hereby corrected as shown below:

Column 1, line 11, delete "sesmi" and substitute

---semi---.

Column 3, line 29, delete "has".

Column 3, line 30, delete "acidicy" and substitue

---acidity---.

Signed and Sealed this

Twenty-eighth Day of December, 1993

*Attest:*

Bruce Lehman

BRUCE LEHMAN

*Attesting Officer*

*Commissioner of Patents and Trademarks*